United States Patent
Gatesoupe et al.

(10) Patent No.: US 8,160,346 B2
(45) Date of Patent: Apr. 17, 2012

(54) METHODS AND APPARATUSES FOR CORRECTING A MAMMOGRAM WITH AN IMPLANT, AND FOR SEGMENTING AN IMPLANT

(75) Inventors: Pascal Gatesoupe, Paris (FR); Sophie Lavoue, Cherbourg-Octeville (FR); Iordache Razvan, Paris (FR); Serge Muller, Guyancourt (FR); Jérôme Durand, Saint-Herblain (FR)

(73) Assignee: General Electric Company, Schenectady, NY (US)

( * ) Notice: Subject to any disclaimer, the term of this patent is extended or adjusted under 35 U.S.C. 154(b) by 1203 days.

(21) Appl. No.: 11/770,101

(22) Filed: Jun. 28, 2007

(65) Prior Publication Data
US 2008/0002872 A1    Jan. 3, 2008

(30) Foreign Application Priority Data
Jun. 30, 2006    (FR) .................................... 06 05915

(51) Int. Cl.
  *G06K 9/00* (2006.01)
  *G06K 9/34* (2006.01)
  *G06K 9/40* (2006.01)
(52) U.S. Cl. ........ 382/132; 382/131; 382/264; 382/173; 378/4
(58) Field of Classification Search .......... 382/128–132, 382/173, 174, 177, 260, 264, 276, 277; 378/4, 378/21; 600/407, 427
See application file for complete search history.

(56) References Cited

U.S. PATENT DOCUMENTS

| | | | | |
|---|---|---|---|---|
| 4,340,911 A | * | 7/1982 | Kato et al. | 382/128 |
| 5,081,580 A | * | 1/1992 | Takeo | 250/582 |
| 5,306,306 A | * | 4/1994 | Bisek et al. | 600/407 |
| 5,458,624 A | * | 10/1995 | Renirie et al. | 607/29 |
| 5,480,439 A | * | 1/1996 | Bisek et al. | 128/898 |
| 5,544,219 A | * | 8/1996 | Muller et al. | 378/210 |
| 5,545,221 A | * | 8/1996 | Hang-Fu | 623/23.67 |
| 5,598,481 A | * | 1/1997 | Nishikawa et al. | 382/130 |
| 5,644,646 A | * | 7/1997 | Du et al. | 382/128 |
| 5,651,042 A | * | 7/1997 | Dewaele | 378/62 |
| 5,666,434 A | * | 9/1997 | Nishikawa et al. | 382/128 |
| 5,673,332 A | * | 9/1997 | Nishikawa et al. | 382/128 |
| 5,740,268 A | * | 4/1998 | Nishikawa et al. | 382/132 |
| 5,941,832 A | * | 8/1999 | Tumey et al. | 600/549 |
| 5,960,102 A | * | 9/1999 | Van Eeuwijk et al. | 382/128 |

(Continued)

OTHER PUBLICATIONS

Changizi et al. "Application of Small Angle Xray Scattering (SAXS) for Differentiation between Normal and Cancerous Breast Tissue" International Journal of Medical Sciences 2005 2(3) pp. 118-121 2005 Ivy Spring International Publisher.*

(Continued)

*Primary Examiner* — Jason M Repko
*Assistant Examiner* — Mia M Thomas
(74) *Attorney, Agent, or Firm* — Global Patent Operation; Jonathan E. Thomas

(57) ABSTRACT

The invention relates to a method of correcting a digital mammogram of a breast containing an implant. According to the invention, brightnesses situated at and around the implant peak (PI) in the low frequency component of the image ($X_{LP}$) are attenuated (ATT) as compared with a function (P1) that is applied to the other brightnesses, thereby attenuating the implant.

The invention also provides a method of segmenting an implant in a radiographic image, the method being characterized by the following steps: smoothing the image by a noise-reducing lowpass filter, applying a non-directional spatial derivative filter, pixel thresholding, and selecting an outline to define the segmented portion of the image that corresponds to the implant.

28 Claims, 4 Drawing Sheets

U.S. PATENT DOCUMENTS

| | | | | |
|---|---|---|---|---|
| 6,072,903 | A * | 6/2000 | Maki et al. | 382/190 |
| 6,075,879 | A * | 6/2000 | Roehrig et al. | 382/132 |
| 6,373,918 | B1 * | 4/2002 | Wiemker et al. | 378/62 |
| 6,385,476 | B1 * | 5/2002 | Osadchy et al. | 600/407 |
| 6,389,305 | B1 * | 5/2002 | Deban et al. | 600/427 |
| 6,724,945 | B1 * | 4/2004 | Yen et al. | 382/274 |
| 6,819,952 | B2 * | 11/2004 | Pfefferbaum et al. | 600/410 |
| 6,885,764 | B2 * | 4/2005 | Wang et al. | 382/131 |
| 6,939,686 | B2 * | 9/2005 | Ling et al. | 435/29 |
| 6,940,520 | B2 * | 9/2005 | Kim et al. | 345/582 |
| 6,956,975 | B2 * | 10/2005 | Young | 382/263 |
| 7,110,602 | B2 * | 9/2006 | Krause | 382/199 |
| 7,245,749 | B2 * | 7/2007 | Okuzawa | 382/128 |
| 7,298,877 | B1 * | 11/2007 | Collins et al. | 382/128 |
| 7,352,887 | B2 * | 4/2008 | Besson | 382/132 |
| 7,386,158 | B2 * | 6/2008 | Yamada | 382/132 |
| 7,388,973 | B2 * | 6/2008 | Fidrich et al. | 382/128 |
| 7,424,138 | B2 * | 9/2008 | Takagi | 382/128 |
| 7,440,609 | B2 * | 10/2008 | Von Berg et al. | 382/154 |
| 7,442,389 | B2 * | 10/2008 | Quelle et al. | 424/489 |
| 7,526,061 | B2 * | 4/2009 | Kobayashi | 378/4 |
| 7,532,997 | B2 * | 5/2009 | Li et al. | 702/150 |
| 7,548,649 | B2 * | 6/2009 | Cardenas et al. | 382/173 |
| 7,551,182 | B2 * | 6/2009 | Bethune et al. | 345/619 |
| 7,598,899 | B2 * | 10/2009 | Allen et al. | 342/25 R |
| 7,756,312 | B2 * | 7/2010 | Hsieh et al. | 382/128 |
| 7,771,716 | B2 * | 8/2010 | Hedrick et al. | 424/93.7 |
| 7,792,339 | B2 * | 9/2010 | Li | 382/128 |
| 7,840,055 | B2 * | 11/2010 | Huo | 382/132 |
| 7,903,850 | B2 * | 3/2011 | Rasch et al. | 382/128 |
| 2001/0016030 | A1 * | 8/2001 | Nicolas et al. | 378/98.11 |
| 2001/0038679 | A1 * | 11/2001 | Muller et al. | 378/37 |
| 2002/0071600 | A1 * | 6/2002 | Yamada | 382/132 |
| 2002/0090052 | A1 * | 7/2002 | Muller et al. | 378/37 |
| 2002/0159565 | A1 * | 10/2002 | Muller et al. | 378/98.12 |
| 2002/0181797 | A1 * | 12/2002 | Young | 382/260 |
| 2003/0009098 | A1 * | 1/2003 | Jack et al. | 600/410 |
| 2003/0095696 | A1 * | 5/2003 | Reeves et al. | 382/131 |
| 2004/0066978 | A1 * | 4/2004 | Nanbu | 382/261 |
| 2004/0114706 | A1 * | 6/2004 | Ikeda et al. | 378/4 |
| 2004/0202360 | A1 * | 10/2004 | Besson | 382/131 |
| 2004/0258325 | A1 * | 12/2004 | Sasada | 382/275 |
| 2005/0100208 | A1 * | 5/2005 | Suzuki et al. | 382/157 |
| 2005/0123178 | A1 * | 6/2005 | Teppaz et al. | 382/128 |
| 2005/0276455 | A1 * | 12/2005 | Fidrich et al. | 382/128 |
| 2006/0165284 | A1 * | 7/2006 | Aharon et al. | 382/173 |
| 2006/0182340 | A1 * | 8/2006 | Cardenas et al. | 382/173 |
| 2006/0204063 | A1 * | 9/2006 | Nakashima et al. | 382/128 |
| 2006/0285745 | A1 * | 12/2006 | Paragios et al. | 382/173 |
| 2006/0291707 | A1 * | 12/2006 | Kothapalli et al. | 382/128 |
| 2008/0095462 | A1 * | 4/2008 | Hsieh et al. | 382/275 |
| 2008/0118123 | A1 * | 5/2008 | Ogura et al. | 382/128 |
| 2009/0185733 | A1 * | 7/2009 | Heinlein et al. | 382/132 |
| 2009/0304151 | A1 * | 12/2009 | Yamada et al. | 378/62 |
| 2009/0306531 | A1 * | 12/2009 | Leuthardt et al. | 600/544 |
| 2010/0027867 | A1 * | 2/2010 | Bernhardt et al. | 382/132 |
| 2010/0195883 | A1 * | 8/2010 | Patriarche et al. | 382/131 |
| 2010/0234719 | A1 * | 9/2010 | Kelly et al. | 600/407 |
| 2010/0246924 | A1 * | 9/2010 | Morita | 382/132 |
| 2010/0278405 | A1 * | 11/2010 | Kakadiaris et al. | 382/131 |
| 2011/0052025 | A1 * | 3/2011 | Highnam et al. | 382/131 |

OTHER PUBLICATIONS

Smith, S. "Zero Crossings of the Laplacian of a Gaussian of the Image Brightness Function" 1997, pp. 1-2.*

Laplacian LOG Filter (2001) http.www.academic.mu.edu/phys pp. 1-3.*

Rieber et al. "Breast Conserving Surgery and Autogenus Tissue Reconstruction in patient with breast cancer: efficacy of MRI of the breast in the detection of recurrent disease" EUR Radiol (2003) 13: 780-787.*

Wang et al. "Supporting Range and Segment Based Hysteresis Thresholding in Edge Detection" ICIP, 2008 pp. 1-4.*

Huertas et al. "Detection of Intensity Changes with Subpixel Accuracy Using Laplacian-Gaussian Masks" IEEE Transactions on Pattern Analysis and Machine Intelligence, vol. PAMI-8 No. 5, Sep. 1996, pp. 1-14.*

Hu et al. "Automatic Lung Segmentation for Accurate Quantitation of Volumetric X-Ray CT Images" IEEE Transactions on Medical Imaging, vol. 20, No. 6 Jun. 2001 pp. 1-9.*

Ahn et al. "Marginal Bone Destructions in Dental Radiography Using Multi-Template Based on Internet Services" Springer-Verlag Berlin Heidelberg (2006) ICCSA, LNCS 3984, pp. 1001-1009.*

Brinkmann et al. "Optimized Homomorphic Unsharp Masking for MR Grayscale Inhomogenity Correction" IEEE Transactions on Medical Imaging vol. 17, No. 2, Apr. 1998 pp. 161-171.*

Ziou, D., and Tabbone, S., "Edge Detection Techniques—An Overview," Pattern Recognition and Image Analysis, vol. 8, No. 4, 1998, pp. 537-559, Allen Press.

Fisher, Robert, Perkins, S., Walker, A., and Wolfart, E., "Sero Crossing Detector," Sep. 11, 2004, URL: http://web.archive.org/web/*/http://homepages.inf.ed.ac.uk/rbf/HIPR2//zeros.htm, Image Processing Learning Resources.

Huertas, Andres, and Medioni, Gerard, "Detection of Intensity Changes with Subpixel Accuracy Using Laplacian—Gaussian Masks," IEEE Transactions on Pattern Analysis and Machine Intelligence, vol. PAMI-8, No. 5, Sep. 1986, pp. 651-664.

Blaffert, T., Dippel, S., Stahl, M., and Wiemker, R., "The Laplace Integral for a Watershed Segmentation," Image Processing, 2000 International Conference on Sep. 10-13, 200, Piscataway, NJ, USA, IEEE, vol. 3, Sep. 10, 2000.

* cited by examiner

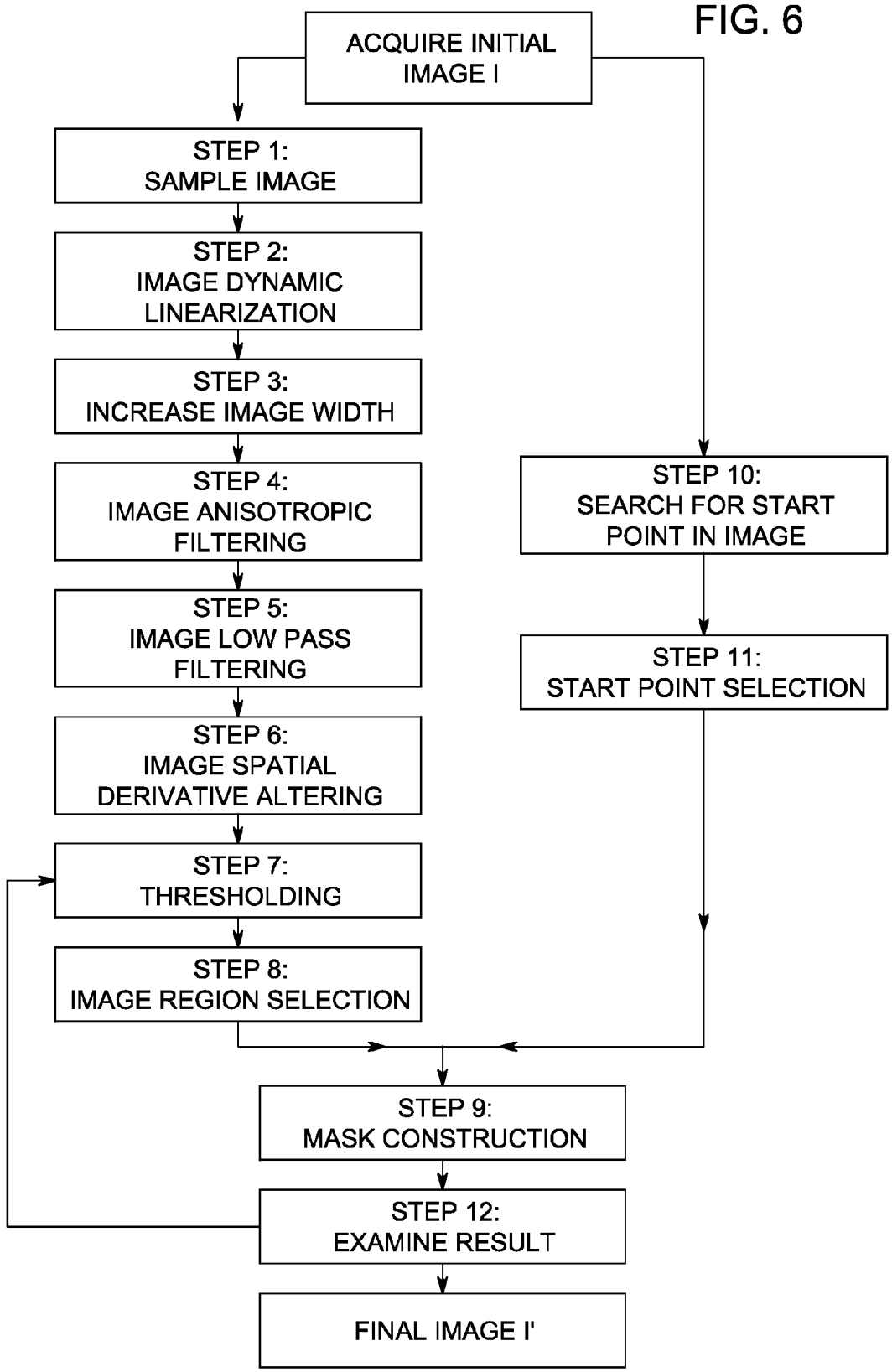

METHODS AND APPARATUSES FOR CORRECTING A MAMMOGRAM WITH AN IMPLANT, AND FOR SEGMENTING AN IMPLANT

FIELD OF THE INVENTION

Embodiments of the he invention provide a method and apparatus for correcting a digital radiographic image of a portion of a patient's body that contains an implant.

The field of application of the invention is medical radiology, and in particular mammography.

In general, the method and the apparatus seek to facilitate the reading of images obtained using a digital imaging technique, so as to enable a practitioner to see at a glance, and if possible without making any adjustments, an image that is clear and well contrasted in all locations.

On such an image, a radiologist should be capable of identifying all clinical signs by perceiving relationships between the various different portions of the image.

Document FR-A-2 847 698 describes a method of managing the dynamic range of a digital radiographic image, in which an image of X-ray thicknesses is filtered by a lowpass filter in order to obtain a context image. The image of X-ray thicknesses is subtracted from the context image in order to obtain an image of details. The context image is processed by a first table computed on the basis of the X-ray thickness image, in order to obtain an image of reduced dynamic range. The context image is also processed by means of a second table computed on the basis of the X-ray thickness image, in order to obtain an image of coefficients, which coefficients are subsequently used for weighting the image of details in order to obtain an image of emphasized details. The reduced dynamic range image and the image with emphasized details are added together, and then compressed in order to make their dynamic range fit within the dynamic range of an imager having a small dynamic range.

That method is well suited to usual X-ray images, in which there does not exist any object that is foreign to the portion of the body being viewed.

However that method suffers from certain limitations when viewing a portion of the body that contains an implant, these limitations preventing it from being applied directly under all circumstances, and possibly also leading to display artifacts.

More and more people are having implants fitted, and in particular more and more women are having breast implants fitted.

In an X-ray image, an implant appears as a zone of brightness, dazzling the radiologist. The dynamic range of known systems is not adapted to an image having an enlarged dynamic range due to the presence of an implant.

In addition, implants can hide tissues situated over or under the implant in the X-ray penetration direction, preventing them from being seen in the X-ray image. An implant attenuates X-rays strongly. Thus, an implant often makes it impossible to have a clear view of mammary tissues, in particular when the implant is a retroglandular silicone implant. A tumor that is covered by an implant can be invisible.

A solution that is often used in practice, consists in pushing back the implant manually so as to take a mammogram of the region of the breast that is left free. Nevertheless, this manipulation has its limits, because it is painful to the woman, it can be dangerous for her, and it runs the risk of rupturing the implant within the breast.

Mammograms are usually taken while compressing the breast between top and bottom plates. Nevertheless, a breast containing an implant cannot be compressed very much, and consequently the mammary tissues are spread out to a smaller extent, thereby producing a superposition of dense zones or microcalcifications, which are then difficult to see in the mammogram.

The quality of images of portions of the body containing an implant is thus not good enough. In particular, with a mammogram, radiologists need more information both concerning the glandular portion of the breast and concerning the zone situated within and around the mammary implant.

In order to view as much mammary tissue as possible, women with mammary implants have four additional mammograms taken, referred to as "Eklund" mammograms, in which the implant is moved by being pushed back against the chest wall while pulling the breast forwards, in order to view more clearly the front portion of the breast. Nevertheless, that method of moving the implant does not provide the expected success with women having contractures, i.e. having hard tissue in the breast around the implant.

SUMMARY OF THE INVENTION

A method and apparatus enabling the drawbacks of the prior art to be mitigated and serving to improve X-ray images of a portion of the body containing one or more implants is disclosed.

Another solution provided by embodiments of the invention for solving the problems caused by opaque foreign objects in X-ray images, e.g. implants, consists in treating independently each object of the image.

The presence of objects needs to be detected in the image in order to identify the type of treatment to be applied to the image. This detection can be performed either by extracting meaningful information from the acquisition system or by shape recognition methods that make use of image processing techniques only.

Thereafter, precise segmentation of the opaque object is applied to the image, taking care not to include other portions of the body within the boundaries of the object, such as portions of breast tissue when dealing with a mammogram of a breast containing an implant.

Finally, each class of object is subjected to independent processing.

The breast should be processed using the usual algorithms.

Objects of no clinical value, such as markers, compressor devices, and devices for positioning by stereotaxy, for example, should either be attenuated, or merely blanked out in order to avoid dazzling the radiologist.

The segmented regions in the image defined as corresponding to the implant can be processed in various ways, for example by being replaced by a black zone or by being attenuated.

If it is desired to mask the implant in the image, it is necessary to detect the exact location of the implant therein. Simple thresholding is found to be insufficient, given that the brightness of the implant is high but can nevertheless be lower than that of certain very dense portions of tissue in the portion of the body being X-rayed, such as, for example, a glandular portion of the breast in a mammogram.

Consequently, an embodiment of the invention provides a more elaborate method of segmentation in order to detect an implant in an X-ray image, and in particular in a mammogram.

In a first aspect, the invention provides a method for correcting a digital mammogram of a breast containing an implant, information being represented in the mammogram by pixels of brightness greater than or less than a background, the method being characterized by performing the following steps in a computer:

detecting, in the histogram of brightnesses of the mammogram, an adipose first peak, calculating a first brightness value corresponding to the adipose first peak, detecting a second peak in the histogram of brightnesses of the mammogram, said second peak corresponding to the presence of the implant, and calculating a second brightness value corresponding to the implant second peak;

resolving the mammogram into a low frequency image component and a high frequency image component;

applying a first correction function to the low frequency image component, in order to obtain a processed low frequency image component, the first correction function comprising:

in the first configuration where breast information is represented in the mammogram by pixels of brightness greater than that of a background, an implant attenuation for brightnesses situated at least at and around the implant peak relative to a first function applied to the other brightnesses situated between the first value and the second value;

in the second configuration in which breast information is represented in the mammogram by pixels having brightnesses lower than that of a background, an implant amplification for brightnesses situated at least at and around the implant peak relative to a first function applied to the other brightnesses situated between the first value and the second value;

restoring the corrected mammogram on the basis of the high frequency component and of the processed low frequency component.

According to other characteristics of the invention:

in the first configuration, the attenuation of the first correction function is applied to the brightnesses of the low frequency image component that are greater than or equal to a predetermined third brightness value lying between the first brightness value of the adipose peak and the second brightness value of the implant peak; and in the second configuration, the amplification of the first correction function is applied to the brightnesses of the low frequency image component that are lower than or equal to a predetermined third brightness value lying between the first brightness value of the adipose peak and the second brightness value of the implant peak.

the third brightness value is calculated as corresponding to the lowest valley detected in the brightness histogram of the mammogram, for brightness values that are less than the second brightness value of the implant peak in the first configuration and that are greater than the second brightness value of the implant peak in the second configuration.

in the first configuration, the attenuation of the first correction function for the low frequency component comprises a decreasing portion for brightnesses lying between the third brightness value and the second brightness value of the implant peak, and a substantially constant portion for brightness values greater than or equal to the second brightness value of the implant peak;

in the second configuration, the amplification of the first correction function of the low frequency component comprises a decreasing portion for brightnesses lying between the third brightness value and the second brightness value of the implant peak, and a substantially constant portion for brightness values less than or equal to the second brightness value of the implant peak.

In the first configuration, the attenuation of the first correction function for the low frequency component includes a substantially constant portion equal to the mean brightness value of the adipose peak divided by the mean brightness value of the implant peak;

in the second configuration, the amplification of the first correction function for the low frequency component includes a substantially constant portion equal to the mean brightness value of the adipose peak divided by the mean brightness value of the implant peak.

Said first correction function for the low frequency component includes a plateau multiplying brightness values lying between the first brightness value of the adipose peak and the third brightness value by a coefficient that is substantially constant.

The first correction function for the low frequency image component includes:

in the first configuration, a raising for brightness values that are less than the first value of the adipose peak;

in the second configuration, additional attenuation for brightness values greater than the first value of the adipose peak.

In the first configuration, the raising is a decreasing function for brightness values less than the first value of the adipose peak;

in the second configuration, the additional attenuation is a decreasing function for brightness values greater than the first value of the adipose peak.

A second correction function is applied to the high frequency image component in order to obtain a processed high frequency image component, the second correction function comprising:

in the first configuration, an attenuation for brightness values less than or equal to the first brightness value of the adipose peak relative to a second function applied to brightness values greater than said first brightness value;

in the second configuration, an amplification for brightness values greater than or equal to the first brightness value of the adipose peak relative to a second function applied to brightness values that are less than said first brightness value.

The invention also provides an apparatus for correcting a digital mammogram of a breast containing an implant, information being represented in the mammogram by pixels having brightnesses that are higher or lower than a background, the apparatus being characterized in that it comprises a computer having:

means for detecting in the brightness histogram of the mammogram, an adipose first peak, means for calculating a first brightness value corresponding to the adipose first peak, means for detecting in the brightness histogram of the mammogram, a second peak corresponding to the presence of the implant, and means for calculating a second brightness value corresponding to the implant second peak;

means for resolving the mammogram into a low frequency image component and into a high frequency image component;

means for applying a first correction function to the low frequency image component in order to obtain a processed low frequency image component, the first correction function comprising:

in the first configuration where breast information is represented in the mammogram by pixels of brightness greater than that of a background, an implant attenuation for brightnesses situated at and around the implant peak relative to a first function applied to the other brightnesses situated between the first value and the second value;

in the second configuration in which breast information is represented in the mammogram by pixels having brightnesses lower than a background, an implant amplification for brightnesses situated at least at and around the implant peak relative to a first function applied to the other brightnesses situated between the first value and the second value; and means for restoring the corrected mammogram on the basis of the high frequency component and of the processed low frequency component.

In a second aspect, the invention provides a method of segmenting an implant in a radiographic image of a portion of a patient's body that contains said implant, to enable the segmented portion of the image corresponding to the implant to be processed subsequently, the method being characterized in that it comprises the following steps performed by a computer:

smoothing the image by a lowpass first filter for reducing noise, in order to obtain a smoothed image;

applying a non-directional spatial derivative second filter to the smoothed image, in order to obtain a filtered image;

thresholding pixels of the filtered image that are above a high first threshold and/or below a low second threshold, in order to obtain a thresholded image; and selecting at least one outline obtained in the thresholded image, in order to define the segmented portion of the image corresponding to the implant.

According to other characteristics of the invention:

The image smoothing is performed by a Gaussian lowpass first filter.

The non-directional spatial derivative second filter applied to the smoothed image is a Laplacian filter.

The image smoothing is performed by a Gaussian lowpass first filter, and the non-directional spatial derivative second filter applied to the smoothed image is a Laplacian filter, the Gaussian first filter and the Laplacian second filter together forming a global LoG filter implementing the following function:

$$LoG(x, y) = -\frac{1}{\pi\sigma^4}\left[1 - \frac{x^2 + y^2}{2\sigma^2}\right]e^{\frac{x^2+y^2}{2\sigma^2}}$$

where x and y are respectively the abscissa and the ordinate of the pixels in the image, and $\sigma$ is the standard deviation of the Gaussian filter.

Zero-crossings are looked for in the filtered image, as subjected to the gradient norm calculated on said filtered image, in order to preselect at least one outline.

The thresholding of the filtered image is hysteresis thresholding, comprising a high first threshold and a low second threshold, the thresholding of the filtered image comprising retaining pixels having a brightness value greater than or equal to the high first threshold, discarding pixels having a brightness value less than the low second threshold, and retaining pixels having a brightness value lying between the high first threshold and the low second threshold providing they are adjacent to at least one pixel having a brightness value greater than or equal to the high first threshold.

The threshold(s) used during the thresholding step is/are modified if the segmented portion that is obtained does not satisfy at least one calculated criterion, and reapplying the thresholding and selection steps in order to obtain a new segmented portion.

Said threshold modification includes at least modifying the low second threshold.

If said criterion is not satisfied after a predetermined number of modifications or after lowering the low second threshold down to a minimum, then dilatations are performed followed by erosions of increasing size on the thresholded image until a closed outline is obtained for defining the segmented portion.

The criterion is at least one of the group constituted by:

the area of the segmented portion belongs to a range of areas relative to the estimated area of the portion of the body in the image;

the variance of the segmented portion is below a variance threshold.

The step of selecting at least one outline obtained in the thresholded image is performed automatically by comparison with region models defined by prerecorded reference functions.

Processing is applied to the resulting segmented image portion, which processing consists in applying a mask for blocking out said segmented portion from the initial image.

Processing is applied to the resulting segmented portion of the image, which processing consists in identifying its outline in the initial image.

Prior to the smoothing step, a dynamic linearization step is applied to the image, for expanding the dynamic range of pale zones relative to the dynamic range of dark zones in the image.

The dynamic linearization step applies a cumulative distribution function to the histogram of the image.

Prior to the smoothing step, at least one anisotropic filtering step is applied to the image in order to decrease noise.

The anisotropic filtering step applies a filter to the preceding pixels u(s,t) of the image, which filter delivers at the following iteration for the pixel of coordinates s, a new pixel u(s,t+$\Delta$t) of coordinates s, defined by the equation:

$$u(s,t+\Delta t)=u(s,t)+\Delta t^*\mathrm{div}(f(\|\nabla u(s,t)\|)\cdot\nabla u(s,t))$$

where:
$\nabla$ designates the gradient operator;
div designates the divergence operator;
f is a decreasing non-uniformity function; and
$\Delta$t is a positive and non-zero predetermined increment.

The decreasing non-uniformity function f is a Gaussian function.

The new pixel $u_s^{(t+1)}$ of the following iteration is given by:

$$u_s^{(t+1)} = \sum_{p\in 4-V-\{s\}} \Delta t \cdot f(u_p^{(t)} - u_s^{(t)})u_p^{(t)} + u_s^{(t)} \cdot \left(1 - \sum_{p\in 4-V-\{s\}} C_p\right)$$

where:

$$C_p = \Delta t \cdot f(|u_p^{(t)} - u_s^{(t)}|) = \Delta t.e^{-\frac{u_p^{(t)}-u_s^{(t)}}{2k^2}}$$

where:
V is a two-dimensional neighborhood of four pixels;
$u_s^{(t)}$ is the pixel of coordinates s in iteration (t) and
k is a predetermined constant.

The predetermined increment $\Delta$t is greater than 0 and less than 0.25.

A mask region is grown inside the boundaries of the resulting segmented portion, the region being grown from at least one selected starting point, by iterating at least one growth step, each growth step including within the mask region those pixels that are adjacent to the region obtained at the preceding iteration and that have brightness values that are sufficiently close to those of the region obtained at the preceding iteration.

The starting point for growth of the mask region is obtained by:

simple thresholding of the image above a brightness threshold that is less than the maximum brightness of the pixels of the image so as to obtain a first image zone;

erosion and then dilatation of the first zone so as to obtain a second zone, with the center of gravity of the second zone then being taken as the starting point for growing the mask region.

The invention also provides an apparatus for segmenting an implant in a radiographic image of a portion of a patient's body containing the implant, to enable the segmented portion of the image corresponding to the implant to be processed subsequently, the apparatus being characterized in that it comprises a computer including means for implementing the segmentation method as described above.

BRIEF DESCRIPTION OF THE DRAWINGS

Embodiments of the invention can be better understood on reading the following description given purely by way of non-limiting example with reference to the accompanying drawings, in which:

FIG. 6 is a flow chart of a preferred implementation of the method of the invention for segmenting an X-ray image.

DETAILED DESCRIPTION

Figure 1:
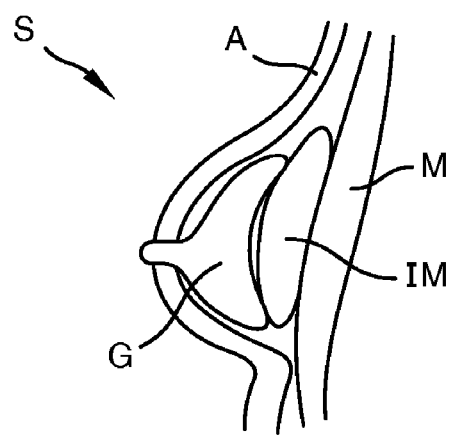
FIG. 1 is a diagrammatic vertical section view showing a breast containing an implant.

In FIG. 1, a breast S comprises subcutaneous adipose tissue A and, in front of the pectoral muscle M and behind glandular tissues G, a mammary implant IM.

The implant IM may be of various types. The implant IM may be a silicone prosthesis comprising an elastomer bag prefilled with a clear, sticky, and thick silicone gel of consistency similar to that of mammary tissue, with a surface that is smooth or rough, and if rough, that is textured in order to reduce the quantity of capsular contractures, for example.

The implant IM may also contain physiological serum, containing a sterilized saline solution.

The implant IM may also have two bags one inside the other. By way of example, the inner bag is prefilled with silicone gel and the outer bag is filled with saline solution, or vice versa. These implants are known as "double lumen" implants.

The mammogram of the breast is taken using conventional X-ray equipment that produces a digital image.

Figure 2:
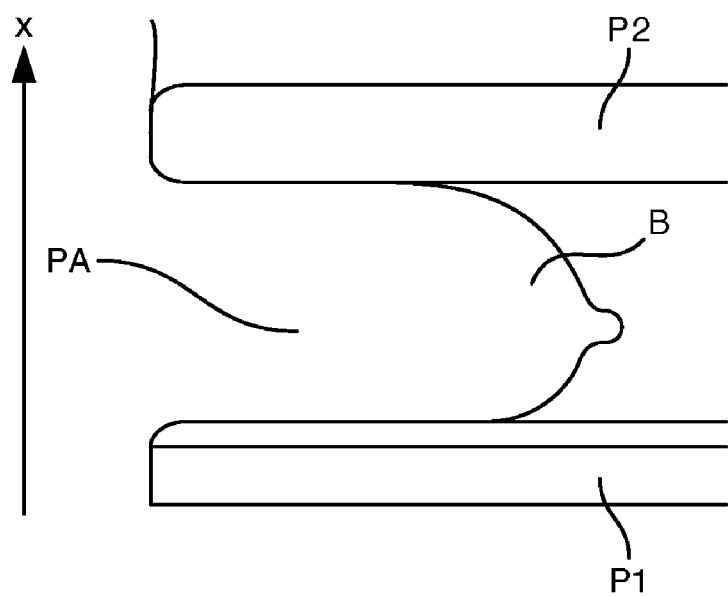
FIG. 2 is a vertical section view of a device used for compressing the breast in order to take a mammogram.

In radiology, the image acquisition phenomenon is of the $I=I_0\exp(-\mu x)$ type, where I is the raw brightness, $I_0$ is a constant, x is the radiological thickness, i.e. the thickness of the breast through the X-rays pass, and $\mu$ is the radiological density at each pixel of the image. I is the signal as actually measured by an electronic radiological detector, or possibly as read from a digitized X-ray image. By way of example and as shown in FIG. 2, the breast is compressed between a top plate P2 and a bottom plate P1 so as to have constant thickness x between the plates P2 and P1 over the rear portion PA of the breast situated close to the muscle M, i.e. with the exception of its front end B. X-rays are directed along the radiological thickness direction x, going from the plate P2 towards the plate P1.

This gives $\mu x=\ln(I_0)-\ln(I)$, where ln is the neperian logarithm function.

In a preferred implementation, the raw brightness image I acquired by the equipment is transformed by a circuit 9 into a radiological thickness image X in the direction x traveled by the X-rays, using the equation:

$$X=-\ln(I)+\ln(I_0)$$

This image X transformed by the function (−ln) is the image that is processed below. In this image X, information concerning the breast is represented by brightnesses brighter than a black background that appears in the absence of any portion of the body being X-rayed, and this constitutes a first configuration in which the invention can be applied.

Naturally, insofar as the transformation performed by the circuit 9 is monotonic, the processing performed on the transformed image X could also be performed directly on the raw image I, while making the corresponding adaptations. In this second configuration using the raw image I, breast information is represented by brightnesses that are darker than a white background that appears in the absence of any portion of the X-rayed body.

Insofar as the transformation performed on the raw image I of brightnesses in order to obtain the image X of radiological thicknesses is a decreasing function, any amplification of the image X after transformation amounts to attenuating the raw image I that has not been transformed, and any attenuation of the transformed image X amounts to amplifying the raw image I that has not been transformed, with the order of brightnesses being inverted between the non-transformed raw image I and the image X of radiological thicknesses.

Figure 3:
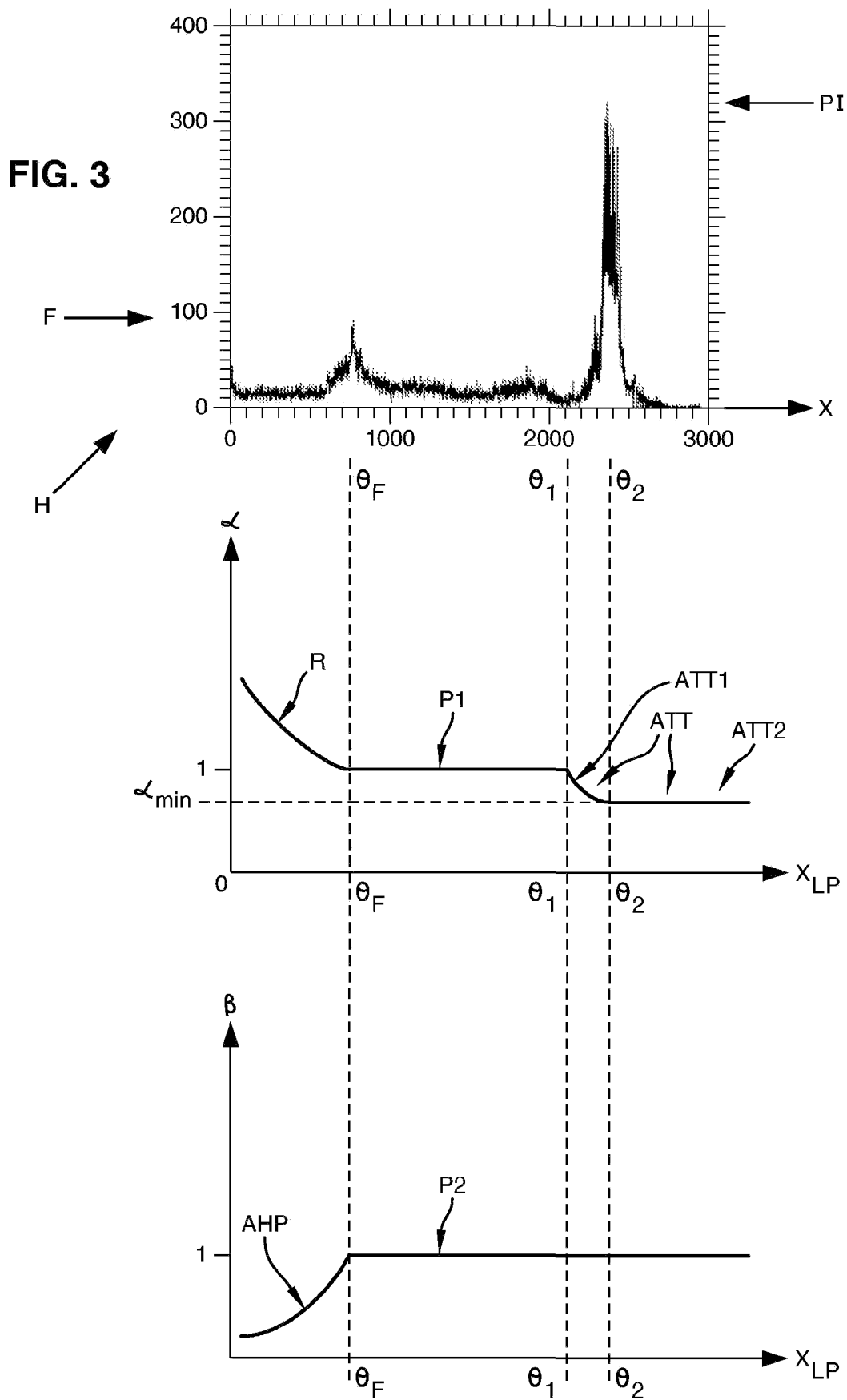
FIG. 3 is a histogram of brightnesses of a mammogram of a breast containing an implant, together with functions used for correcting the mammogram.

In FIG. 3, the brightnesses values in the image X of radiological thicknesses are plotted along the abscissa of the histogram H at the top of FIG. 3 and are referred to as the brightnesses X of the mammogram in the description below, which applies to the first above-mentioned configuration.

The histogram H of brightnesses X is calculated automatically by any suitable calculation means, such as the processor of a computer.

The calculation means includes means for detecting a first peak F in the histogram H corresponding to adipose tissue A, and means for detecting a second peak PI in the histogram H corresponding to the implant IM. The adipose first peak F serves to obtain a first brightness value $\theta_F$ corresponding to said peak F, and the implant second peak PI serves to obtain a second brightness value $\theta_2$ corresponding to the second peak PI. The second brightness value $\theta_2$ of the implant peak PI is greater than the first value $\theta_F$ of the adipose peak, the peak PI being higher than the peak F, for example.

The implant peak PI is determined, for example, by the fact that it corresponds to the highest peak in the histogram H, and to the brightness value $\theta_2$ that is the highest amongst the tall peaks detected in the histogram H.

The image X is resolved into a low frequency component $X_{LP}$ and a high frequency component $X_{HP}$.

Figure 4:
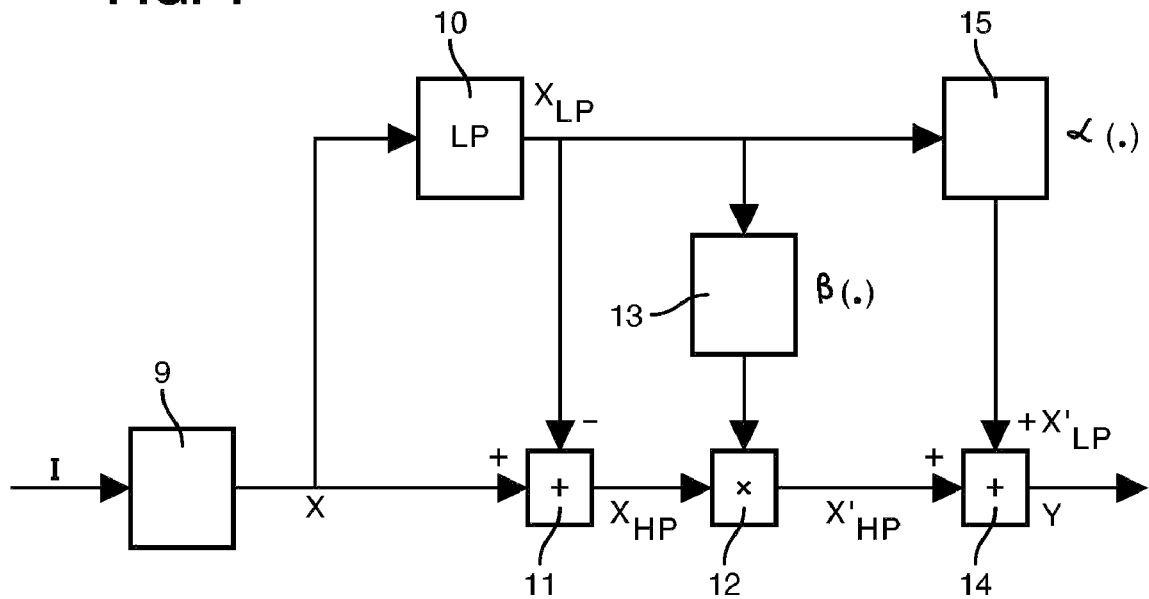
FIG. 4 is a modular summary of the various steps implemented in the correction method and apparatus of the invention.

For example, in the embodiment shown in FIG. 4, the image X is applied to a spatial lowpass filter 10, producing a context image $X_{LP}$ from the image X. The context image $X_{LP}$ is applied to the inverting input of a subtracter 11 whose non-inverting input receives the image X, so as to output a high frequency image component $X_{HP}$ satisfying the equation:

$$X=X_{LP}+X_{HP}$$

The low frequency image component $X_{LP}$ is delivered to a filter 15 that applies a first correction function, written $\alpha$ in the figures, to the pixels of this low frequency image component $X_{LP}$.

This first correction function $\alpha$ comprises attenuating ATT those brightness values of the low frequency component $X_{LP}$ that have values situated in the vicinity of the second brightness value $\theta_2$ corresponding to the implant peak PI.

In a preferred embodiment, the attenuation ATT is applied to brightness values that are greater than or equal to a determined third brightness value $\theta_1$, itself lying between the first brightness value $\theta_F$ of the adipose peak F, and the second brightness value $\theta_2$ of the implant peak PI, being for example closer to the second value $\theta_2$ than to the first value $\theta_F$. By way of example, this third value $\theta_1$ is detected in the histogram H as being situated in the nearest valley or the deepest valley of the implant peak PI lower than the second brightness value $\theta_2$ of said implant peak PI, by using any appropriate means.

The attenuation ATT applied multiplies the brightnesses that are greater than the third value $\theta_1$ by coefficients that are smaller than the coefficient(s) applied to the brightnesses that are less than said third value $\theta_1$.

In a preferred embodiment, the first correction function $\alpha$ applied to the low frequency component $X_{LP}$ of the image X possesses a first plateau P1 of constant value, e.g. substantially equal to 1, that applies substantially no modification to brightness values lying between the first value $\theta_F$ of the adipose peak F and the third brightness value $\theta_1$.

By way of example, this attenuation function ATT is made up of a decreasing function ATT1 going from the third brightness value $\theta_1$ to the second brightness value $\theta_2$ of the implant peak PI, and of a substantially constant function ATT2 equal to $\alpha_{min}$ for brightness values greater than or equal to the second value $\theta_2$ of the implant peak PI, this constant function $\alpha_{min}$ being less than the multiplicative coefficient of the plateau P1 (equal to 1 in the above example) that is applied between the first value $\theta_F$ and the third value $\theta_1$.

In a preferred embodiment, the minimum correction value $\alpha_{min}$ applied to the low frequency component $X_{LP}$ is equal to the mean value of brightnesses in the adipose peak F, substantially equal or equal to the first brightness value $\theta_F$, divided by the second brightness value $\theta_2$ of the implant peak PI, using the following equation:

$$\alpha_{min}=\theta_F/\theta_2$$

Figure 5:
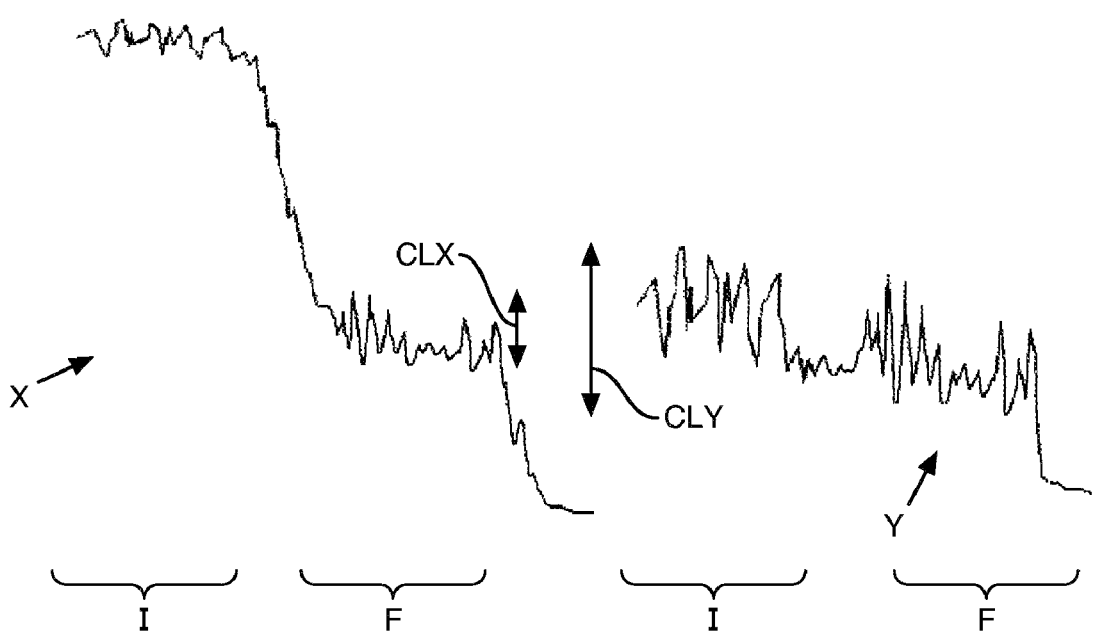
FIG. 5 is a diagram having brightnesses plotted up the ordinate at various locations in the mammogram plotted along the abscissa, on the left prior to processing by the correction method of the invention, and on the right after processing by the correction method of the invention.

As shown in the left-hand portion of FIG. 5, the pixels of the implant IM in the image X have brightnesses that are much greater than neighboring pixels belonging to adipose tissue F.

The attenuation function ATT serves to reduce the pixels of the implant IM to brightnesses that are generally at the same level as those of pixels of adipose tissue F, as shown in the right-hand portion of FIG. 5.

In a preferred embodiment of the invention, the correction function $\alpha$ also includes a raising R (emphasizing) of brightnesses that are situated below the first brightness value $\theta_F$ of the adipose peak F. This compensates for the decrease in thickness of the front end B of the breast.

The module 15 multiplies the low frequency component $X_{LP}$ by the correction function $\alpha$, as a function of the value of the brightnesses of the pixels in $X_{LP}$, so as to obtain a processed low frequency image component $X'_{LP}$.

The high frequency component $X_{HP}$ of the image is also processed by means of a second correction function $\beta$ that is determined in a correction filter 13 whose input receives the low frequency component $X_{LP}$.

The values taken by the second correction function $\beta$ for each pixel of the high frequency component $X_{HP}$ of the image are determined in the correction filter 13 as a function of the brightness value at the location of each pixel in the low frequency component $X_{LP}$.

At each pixel P of the high frequency image $X_{HP}$, the high frequency component $X_{HP}$ is thus processed by the function $\beta$ in application of the following equation:

$$X'_{HP}(P)=\beta(X_{LP}(P))\cdot X_{HP}(P)$$

By way of example, this second correction function $\beta(X_{LP})$ comprises an attenuation function, e.g. an increasing function, for brightness values in the low frequency component $X_{LP}$ that are less than the first value $\theta_F$ of the adipose peak F, as compared with a second plateau P2 that is constant and for example equal to 1 for brightness values that are greater than or equal to said first value $\theta_F$ of the adipose peak F.

The brightness values of the pixels in the high frequency component $X_{HP}$ of the image are multiplied by said second correction function $\beta$ taken from the filter 13 in a multiplier module 12 in order to obtain a processed high frequency component $X'_{HP}$ of the image.

$\alpha$ depends on $X_{LP}$ and $\beta$ depends on $X_{HP}$, with the values of $\alpha$ and $\beta$ being, for example, prerecorded in look-up tables (LUT) in the modules 15 and 13.

Thereafter, the processed low frequency component $X'_{LP}$ and the processed high frequency component $X'_{HP}$ are added in an adder 14 in order to deliver a corrected mammogram image Y.

This gives $Y=\alpha\cdot X_{LP}+\beta\cdot X_{HP}$.

It can be seen from the right-hand portion of FIG. 5 that in the resulting image Y, the brightness of the implant IM is decreased, while local contrast, both in the implant IM and in the adipose tissue A (local contrast CLY for the image Y in the right-hand portion of FIG. 5), is increased relative to the image X (local contrast CLX for the image X in the left-hand portion of FIG. 5).

Thereafter, the mammogram is reproduced on the basis of the processed image Y by any appropriate means. For this purpose, the mammogram may be displayed on a screen, recorded, etc.

The first correction function $\alpha$ for the low frequency component $X_{LP}$ is, for example, a function that decreases as a function of brightness values, while the second correction function $\beta$ for the high frequency component $X_{HP}$ is a function that is non-decreasing as a function of the values of the low frequency component $X_{LP}$.

In the implementation of the segmentation method shown in FIG. 6, the image I acquired by a conventional X-ray system is initially under-sampled, e.g. by a factor of 4, during a first step S1.

Thereafter, during a second step S2, the image is subjected to dynamic linearization.

The brightness that appears in a mammogram or an X-ray image is calculated using the formula:

$$I = \int e^{-\lambda x} dx$$

which leads to a small dynamic range for strong signals.

The purpose of linearization is to flatten the histogram of brightnesses in the image. For an image that presents a peak in pale levels, as applies for the implant peak PI, linearization extends the dynamic range of the pale zone to the detriment of the dynamic range of the dark zone. The transformation that gives the best approach to a uniform distribution of brightness values can be obtained by a cumulative distribution function (cdf) or cumulative histogram, i.e. the integral of the original histogram of the X-ray image.

The linearization procedure can be summed up as follows:

$$g'(x,y) = (g_{max} - g_{min}) P(g(x,y)) + g_{min}$$

where g is the original radiographic image, $P(g(x,y))$ is the cumulative distribution function of g, and $g_{min}$ and $g_{max}$ are the extreme gray levels of g.

Thereafter, during a third step S3, the width of the image is increased in order to limit edge effects during subsequent filtering. The image is padded out to left and to right by repeating the first and last columns of the initial image.

A fourth step S4 is then performed during which image noise is eliminated by anisotropic filtering. Anisotropic filtering is a non-linear smoothing method that serves to remove non-meaningful details while preserving outlines.

By way of example, the anisotropic filter operates on the principle of seeking to reproduce the phenomenon of anisotropic heat diffusion, so as to preserve contrast in the image, using the following equation:

$$\frac{\partial u(s,t)}{\partial t} = div(f(\|\nabla u(s,t)\|) \cdot \nabla u(s,t))$$

where:
  $\nabla$ is the gradient operator and div designates the divergence operator, i.e. the sum of the partial derivative; and
  f models a non-uniformity function of the propagation domain, s represents a site in three dimensions, t represents time, and u represents the quantity of heat.

In order to conserve outlines as well as possible, it is preferable to select a function f that is a decreasing function, leading to weak smoothing in the vicinity of outlines (high gradient) and strong smoothing otherwise (low gradient and low divergence).

In a low gradient zone, the operator will tend to function as a linear filter of extended impulse response, whereas conversely in a high gradient zone, the equivalent impulse response is concentrated about the origin.

The time-discretized equation for heat propagation gives rise to the following iterative calculation:

$$u(s, t+\Delta t) = u(s,t) + \Delta t \cdot div(f(\|\nabla u(s,t)\|) \cdot \nabla u(s,t))$$

By discretizing the differential operators over a neighborhood V, e.g. four pixels in a two-dimensional neighborhood, and by using a Gaussian function for the function f, the filter equation becomes:

$$u_s^{(t+1)} = u_s^{(t)} + \Delta t \cdot [f(u^{(t)}(i-1,j) - u_s^{(t)})(u^{(t)}(i-1,j) - u_s^{(t)})] +$$
$$\Delta t \cdot [f(u^{(t)}(i+1,j) - u_s^{(t)})(u^{(t)}(i+1,j) - u_s^{(t)})] +$$
$$\Delta t \cdot [f(u^{(t)}(i,j-1) - u_s^{(t)})(u^{(t)}(i,j-1) - u_s^{(t)})] +$$
$$\Delta t \cdot [f(u^{(t)}(i,j+1) - u_s^{(t)})(u^{(t)}(i,j+1) - u_s^{(t)})]$$

Using the following conventions: s=(i,j) in two dimensions and $u_s^{(t)} = u^{(t)}(i,j)$ $$u_s^{(t+1)} = \sum_{p \in 4-V-\{s\}} \Delta t \cdot f(u_p^{(t)} - u_s^{(t)}) u_p^{(t)} + u_s^{(t)} \cdot \left(1 - \sum_{p \in 4-V-\{s\}} C_p\right)$$

with $$C_p = \Delta t \cdot f(|u_p^{(t)} - u_s^{(t)}|)$$

If a Gaussian function is selected for f, then the following is obtained:

$$C_p = \Delta t \cdot e^{\frac{u_p^{(t)} - u_s^{(t)}}{2k^2}}$$

The parameter k is the order of the amplitude of the outlines to be preserved.

$\Delta t$ is less than 0.25 to ensure that the result is stable.

(t) represents the $t^{th}$ iteration of filtering the pixel u(i,j).

s=(i,j) being the two-dimensional coordinates of the pixel u.

The anisotropic filtering of the pixels of the image is performed over a plurality of successive iterations, e.g. at least ten, so that the result of the filtering becomes visible.

Thereafter, during a fifth step S5, the image is filtered by a lowpass filter so as to be smoothed in order to improve noise immunity. This is done by means of filtering with a Gaussian filter, for example.

During the following step S6, the image is filtered again in a spatial derivative filter. This spatial derivative filter is non-directional, so as to give outlines that are independent of orientation, unlike first order derivative operators that are directional.

The steps S5 and S6 may also be performed simultaneously.

This non-directional spatial derivative filter is constituted for example by a Laplacian, using the second derivative of the image, in application of the following formula:

$$L(x,y) = \nabla^2 f(x,y) = \frac{\partial^2 f(x,y)}{\partial x^2} + \frac{\partial^2 f(x,y)}{\partial y^2}$$

In a preferred embodiment, when the smoothing of step S5 is performed with a Gaussian filter and when step S6 applies a Laplacian filter, the steps S5 and S6 together apply a global LoG filter to the image, i.e. Laplacian on Gaussian filtering, which is calculated as follows:

$$LoG(x,y) = -\frac{1}{\pi \sigma^4}\left[1 - \frac{x^2 + y^2}{2\sigma^2}\right] e^{-\frac{x^2+y^2}{2\sigma^2}}$$

where x and y are respectively the abscissa and the ordinate of the pixels in the image and σ is the standard deviation of the Gaussian filter.

Thereafter, the image filtered during steps S5 and S6 can be approximated by a convolution mask, that can have dimensions 9×9 in the above-described preferred example.

Where the image is uniform, the LoG filter gives zero. Wherever there is any variation, the LoG filter gives a positive response on the darker side and a negative response on the paler side.

Thereafter, it is possible to look for crossings near zero in the filtered image, that have been subjected to the gradient norm previously calculated on said filtered image.

These zero-crossings are preselected or added as outlines in the image, prior to step S7.

Then, during step S7, thresholding is applied to the filtered image, e.g. thresholding by hysteresis. This thresholding technique uses two thresholds: a high threshold and a low threshold. Below the low threshold, it is assumed that this is not an outline. Above the high threshold, it is assumed that there is certainly an outline. Between the high threshold and the low threshold, only those pixels that are adjacent to an outline pixel that is itself certain are retained as new outline pixels, i.e. the pixels that are retained are those that are adjacent to a pixel that is situated above the high threshold. The low threshold provides immunity against noise and the high threshold serves to eliminate false outlines that might be detected.

In the preferred embodiment shown in FIG. 6, the high threshold and/or the low threshold can be modified in order to restart step S7.

Step S7 is followed by a selection step S8, during which regions that are not likely to correspond to an outline of the implant are eliminated. For example, to do this, connected regions that are too small are eliminated, since these represent small regions that are not meaningful, and possibly the largest connected region is also eliminated if it is too large. Only those regions that touch the edge of the image corresponding to the right- or left-hand side thereof, and spaced apart by a distance that is sufficient to correspond with an implant, are retained.

In a preferred embodiment, this step S8 of selecting one or more outlines in the thresholded image is performed automatically by comparing the regions defined by outlines present in the thresholded image with models of regions defined by reference functions, e.g. corresponding to implants of different types and shapes, or corresponding to biopsy needles having characteristic side, length, and mean brightness. An implant IM is recognized in an outline of the thresholded image, and the outline is retained, e.g. if the function applied to said outline takes on a maximum value.

During step S8, one or more outlines present in the thresholded image is/are selected in order to define the region corresponding to the implant IM.

Thereafter, the portion of the image that is defined in this way and that is assumed to correspond to the implant IM is processed. Below, and in preferred manner, this processing consists in applying a mask to the region of the implant as defined by the selected outlines.

During following step S9 of the processing, a mask is constructed by growing the region inside the outline(s) defining the region or segmented portion of the implant.

This region growth operates as follows, for example:

A starting point is selected in step S11 that belongs to the region concerned in the image I.

The brightness values of pixels adjacent to this starting point are then examined. If the values of the pixels adjacent to the starting point are close enough to the brightness value of said starting point, then the new pixels are included in the region. The process is then repeated step by step for the pixels adjacent to the pixels already included in the region.

Growth is stopped when the pixels adjacent to the region no longer present sufficient similarity with those already present in the region.

In order to find the starting point in the image I at which to start growing a region, a search is made initially during a step S10 preceding step S11 for the first zone determined in the image I by simple thresholding above a brightness value threshold:

$$THR = \max(\text{image}) - \delta$$

where:

max(image) is the maximum of the pixel brightness values in the image, and δ is a predetermined non-zero positive value.

Thereafter, an opening of size 5 is made in the first zone in order to be sure of having a connected zone within the implant, where an opening consists in erosion followed by dilatation.

Erosion makes use of a structuring element B, e.g. a rectangle of pixels of predetermined size. Let $B_k$ be the structuring element, centered on a pixel k. Erosion consists in asking for each pixel k in the zone K of an image L the following question: "is the structuring element $B_k$ fully contained within the zone K?"

The set of positions k of the zone K corresponding to a positive reply (yes), i.e. the pixels k of the zone K for which the structuring element $B_k$ is contained entirely within the zone K, forms the new set K', said to be eroded from K by B, and satisfying the following equation:

$$K' = \{k \in K : B_k \subset K\}$$

Erosion is written $E^B$, where $$K' = E^B(K)$$

Dilatation is the dual of the erosion operation.

Taking the same structuring element $B_k$, the following question is asked for each pixel k: "does the structuring element $B_k$ touch the set K?", i.e. is there a non-empty intersection between $B_k$ and the zone K?

The set of pixels in the image L corresponding to positive responses (yes), i.e. the pixels k of the image L for which the structuring element $B_k$ presents a non-empty intersection with the zone K forms the new set K" dilated from K:

$$K'' = \{k \in L : B_x \cap X \neq \emptyset\}$$

The dilatation operation is written $D^B$ where:

$$K'' = D^B(K)$$

During step S11, the center of gravity of the second zone as found by means of said opening is taken as the starting point for growth, which starting point is then certain to be situated within the implant.

During step S7, hysteresis thresholding gives results between −1 and 0, where −1 represents outlines. During processing step S9, the region growth function is applied to the image obtained from selection step S8, by determining the range in which the region is to remain, e.g. −0.9999 to 0. This produces a new segmented portion of the image that ought to correspond to the implant.

Thereafter, during step S12, the quality of the result obtained by the preceding processing step S9 is examined.

If it is found that the result is not good, on the basis of one or more criteria calculated on the resulting segmented portion, one or more of the thresholds used in the thresholding of step S7 is/are modified, e.g. in preferred manner the low threshold, and steps S7, S8, and S9 are reiterated with this new adjustment of the threshold(s).

The criteria or criterion used for evaluating the quality of the segmented region that is supposed to correspond to the implant may be as follows:

- the area of the segmented region, which should lie within a range of values relative to the area of the portion of the body, for example in a mammogram it should lie within 0.15 times the area of the breast to 0.8 times the area of the breast. When the area of the segmented region does not lie in this range, the segmented region does not correspond to the implant, in which case the high threshold for hysteresis thresholding is decreased;
- the variance of the segmented region in the initial image I. If this variance is too great, then the segmented region includes a region in addition to the implant;
- the minimum value of the segmented region;
- the difference between the maximum value and the minimum value in the segmented region.

So long as one or other of these criteria continues to be unsatisfied, the low threshold for hysteresis thresholding is decreased.

If the criteria are still not satisfied after lowering the low threshold of hysteresis thresholding as far as possible, or after some predetermined number of modifications to the threshold(s), it is possible to return to the initial thresholds or possibly to reduce the high threshold a little, and perform closures of increasing size on the thresholded image in order to obtain a closed outline.

A closure consists in a dilatation followed by an erosion.

Finally, it can happen that the image is taken in costal profile, i.e. bones of the chest can be seen in the mammogram, as well as the entire implant. Under such circumstances, it is difficult to separate the implant from the ribs which also present very high brightness. In addition, for this type of image, the implant is offset from the edge of the image. Under such circumstances, it is not possible to select only those outlines that touch the edges of the image, and that complicates selecting a region that is likely to correspond to the implant.

When step S12 makes it possible to determine that the image processed by step S9 is of sufficient quality, the segmented portion forming a dark mask is superposed on the initial image I, this masked region corresponding to the implant IM in the initial image I and blocking out the implant from the final image I'.

The processed image can then be reproduced by any appropriate means, e.g. by being displayed on the screen, recorded, etc.

In an embodiment, the segmentation method and then the correction method are implemented in order to process the same initial image. Thus, the invention also provides a segmentation and correction method. Similarly, an embodiment of the apparatus of the invention is apparatus for performing both segmentation and correction, comprising both said means mentioned for the segmentation apparatus and said means mentioned for the correction apparatus.

The invention clamed is:

1. A method of segmenting an implant in a radiographic image of a portion of a patient's body that contains the implant, the method comprising:
   (a) smoothing the image by a lowpass first filter for reducing noise in order to obtain a smoothed image;
   (b) applying a non-directional spatial derivative second filter to the smoothed image in order to obtain a filtered image;
   (c) hysteresis thresholding pixels of the filtered image in order to obtain a thresholded image, the hysteresis thresholding comprising:
      (i) retaining pixels having a brightness value greater than or equal to a high first threshold,
      (ii) discarding pixels having a brightness value less than a low second threshold, and
      (iii) retaining pixels having a brightness value lying between the high first threshold and the low second threshold providing they are adjacent to at least one pixel having a brightness value greater than or equal to the high first threshold;
   (d) selecting an outline obtained in the thresholded image, thereby defining a segmented portion of the image corresponding to the implant;
   (e) modifying the low second threshold used during the hysteresis thresholding if the segmented portion obtained does not satisfy a calculated criterion, and reapplying the hysteresis thresholding and electing an outline in order to obtain a new segmented portion of the image; and
   if the calculated criterion is not satisfied after a predetermined number of modifications or after lowering the low second threshold to a minimum, then dilatations are performed followed by erosions of increasing size on the thresholded image until a closed outline is obtained defining the segmented portion,
   wherein prior to the smoothing at least one anisotropic filtering is applied to the image in order to decrease noise, and
   wherein the anisotropic filtering applies a filter to the preceding pixels of the image, which filter delivers at the following iteration for the pixel of coordinates s, a new pixel of coordinates s, defined by the equation:

$$u(s,t+\Delta t)=u(s,t)+\Delta t^*\text{div}\,(f(\|\nabla u(s,t)\|)\cdot\nabla u(s,t))$$

where:
   $\nabla$ designates the gradient operator;
   div designates the divergence operator;
   f is a decreasing non-uniformity function; and
   $\Delta t$ is a positive and non-zero predetermined increment.

2. The method according to claim 1, wherein the image smoothing is performed by a Gaussian lowpass first filter.

3. The method according to claim 1, wherein the non-directional spatial derivative second filter applied to the smoothed image is a Laplacian filter.

4. The method according to claim 1, wherein the image smoothing is performed by a Gaussian lowpass first filter, and the non-directional spatial derivative second filter applied to the smoothed image is a Laplacian filter, the Gaussian first filter and the Laplacian second filter together forming a global LoG filter implementing the following function:

$$LoG(x,y) = -\frac{1}{\pi\sigma^4}\left[1-\frac{x^2+y^2}{2\sigma^2}\right]e^{-\frac{x^2+y^2}{2\sigma^2}}$$

where x and y are respectively the abscissa and the ordinate of the pixels in the image, and σ is the standard deviation of the Gaussian filter.

5. The method according to claim 1, wherein zero-crossings are looked for in the filtered image, as subjected to the gradient norm calculated on said filtered image, in order to preselect at least one outline.

6. The method according to claim 1, wherein the criterion is at least one of the group constituted by:

the area of the segmented portion belongs to a range of areas relative to the estimated area of the portion of the body in the image; and the variance of the segmented portion is below a variance threshold.

7. The method according to claim 1, wherein the selecting at least one outline obtained in the thresholded image is performed automatically by comparison with region models defined by prerecorded reference functions.

8. The method according to claim 1, wherein processing is applied to the resulting segmented image portion, which processing consists in applying a mask for blocking out said segmented portion from the initial image.

9. The method according to claim 1, wherein processing is applied to the resulting segmented portion of the image, which processing consists in identifying its outline in the initial image.

10. The method according to claim 1, wherein prior to the smoothing, a dynamic linearization is applied to the image, for expanding the dynamic range of pale zones relative to the dynamic range of dark zones in the image.

11. The method according to claim 10, wherein the dynamic linearization applies a cumulative distribution function to the histogram of the image.

12. The method according to claim 1 wherein the decreasing non-uniformity function f is a Gaussian function.

13. The method according to claim 12, wherein the new pixel of the following iteration is given by:

$$u_s^{(t+1)} = \sum_{p \in 4-V-\{s\}} \Delta t \cdot f(u_p^{(t)} - u_s^{(t)}) u_p^{(t)} + u_s^{(t)} \cdot \left(1 - \sum_{p \in 4-V-\{s\}} C_p\right)$$

where:

$$C_p = \Delta t \cdot f(|u_p^{(t)} - u_s^{(t)}|) = \Delta t \cdot e^{\frac{u_p^{(t)} - u_s^{(t)}}{2k^2}}$$

where:
V is a two-dimensional neighborhood of four pixels;
$u_s(t)$ is the pixel of coordinates s in iteration (t); and
k is a predetermined constant.

14. The method according to claim 1, wherein the predetermined increment $\Delta t$ is greater than 0 and less than 0.25.

15. The method according to claim 1, wherein a mask region is grown inside the boundaries of the resulting segmented portion, the region being grown from at least one selected starting point, by iterating at least one growth step, each growth step including within the mask region those pixels that are adjacent to the region obtained at the preceding iteration and that have brightness values that are sufficiently close to those of the region obtained at the preceding iteration.

16. The method according to claim 15, wherein the starting point for growth of the mask region is obtained by:
simple thresholding of the image above a brightness threshold that is less than the maximum brightness of the pixels of the image so as to obtain a first image zone; and
eroding and then dilating the first zone so as to obtain a second zone, with the center of gravity of the second zone then being taken as the starting point for growing the mask region.

17. A method of segmenting an implant and for correcting a digital mammogram of a breast containing an implant, information being represented in the mammogram by pixels of brightness greater than or less than a background, the method comprising:

detecting, in the histogram of brightnesses of the mammogram, an adipose first peak, calculating a first brightness value corresponding to the adipose first peak, detecting a second peak in the histogram of brightnesses of the mammogram, said second peak corresponding to the presence of the implant, and calculating a second brightness value corresponding to the implant second peak;

resolving the mammogram into a low frequency image component and a high frequency image component;

applying a first correction function to the low frequency image component, in order to obtain a processed low frequency image component, the first correction function comprising:
in a first configuration where breast information is represented in the mammogram by pixels of brightness greater than that of a background, an implant attenuation for brightnesses situated at least at and around the implant peak relative to a first function applied to the other brightnesses situated between the first value and the second value;
a second configuration in which breast information is represented in the mammogram by pixels having brightnesses lower than that of a background, an implant amplification for brightnesses situated at least at and around the implant peak relative to a first function applied to the other brightnesses situated between the first value and the second value; and restoring the corrected mammogram on the basis of the high frequency component and of the processed low frequency component.

18. The method according to claim 17, wherein:
in the first configuration, the attenuation of the first correction function is applied to the brightnesses of the low frequency image component that are greater than or equal to a predetermined third brightness value lying between the first brightness value of the adipose peak and the second brightness value of the implant peak; and
in the second configuration, the amplification of the first correction function is applied to the brightnesses of the low frequency image component that are lower than or equal to a predetermined third brightness value lying between the first brightness value of the adipose peak and the second brightness value of the implant peak.

19. The method according to claim 18, wherein the third brightness value is calculated as corresponding to the lowest valley detected in the brightness histogram of the mammogram, for brightness values that are less than the second brightness value of the implant peak in the first configuration and that are greater than the second brightness value of the implant peak in the second configuration.

20. The method according to claim 18, wherein:
in the first configuration, the attenuation of the first correction function for the low frequency component comprises a decreasing portion for brightnesses lying between the third brightness value and the second brightness value of the implant peak, and a substantially constant portion for brightness values greater than or equal to the second brightness value of the implant peak; and
in the second configuration, the amplification of the first correction function of the low frequency component comprises a decreasing portion for brightnesses lying between the third brightness value and the second brightness value of the implant peak, and a substantially constant portion for brightness values less than or equal to the second brightness value of the implant peak.

21. The method according to claim 20, wherein:
in the first configuration, the attenuation of the first correction function for the low frequency component includes a substantially constant portion equal to the mean brightness value of the adipose peak divided by the mean brightness value of the implant peak; and
in the second configuration, the amplification of the first correction function for the low frequency component includes a substantially constant portion qual to the mean brightness value of the adipose peak (F) divided by the mean brightness value of the implant peak.

22. The method according to claim 17, wherein said first correction function for the low frequency component includes a plateau multiplying brightness values lying between the first brightness value of the adipose peak and the third brightness value by a coefficient that is substantially constant.

23. The method according to claim 17, wherein the first correction function for the low frequency image component includes:
in the first configuration, a raising for brightness values that are less than the first value of the adipose peak; and
in the second configuration, additional attenuation for brightness values greater than the first value of the adipose peak.

24. The method according to claim 23, wherein:
in the first configuration, the raising is a decreasing function for brightness values less than the first value of the adipose peak; and
in the second configuration, the additional attenuation is a decreasing function for brightness values greater than the first value of the adipose peak.

25. The method according to claim 17, wherein a second correction function is applied to the high frequency image component in order to obtain a processed high frequency image component, the second correction function comprising:
in the first configuration, an attenuation for brightness value less than or equal to the first brightness value of the adipose peak relative to a second function applied to brightness values greater than said first brightness value; and
in the second configuration, an amplification for brightness values greater than or equal to the first brightness value of the adipose peak relative to a second function applied to brightness values that are less than said first brightness value.

26. An apparatus for segmenting an implant and for correcting a mammogram of a breast containing an implant, the apparatus comprising:
means for detecting an adipose first peak in a histogram of pixel brightness of the mammogram;
means for calculating a first brightness value corresponding to the adipose first peak;
means for detecting an implant second peak in the histogram of pixel brightness of the mammogram;
means for calculating a second brightness value corresponding to the implant second peak;
means for separating the mammogram into a low frequency image component and into a high frequency image component;
means for applying a correction function to the low frequency image component in order to obtain a processed low frequency image component; and
means for combining the high frequency component and the processed low frequency component into a corrected mammogram.

27. The apparatus according to claim 26 wherein the correction function attenuates the brightness of pixels at and around the implant second peak in a mammogram where breast information is represented by pixels having a brightness greater than that of a background of the mammogram.

28. The apparatus according to claim 26 wherein the correction function amplifies the brightness of pixels at and around the implant second peak in a mammogram where breast information is represented by pixels having a brightness lower than that of a background of the mammogram.

* * * * *

UNITED STATES PATENT AND TRADEMARK OFFICE
CERTIFICATE OF CORRECTION

PATENT NO. : 8,160,346 B2
APPLICATION NO. : 11/770101
DATED : April 17, 2012
INVENTOR(S) : Gatesoupe et al.

Page 1 of 1

It is certified that error appears in the above-identified patent and that said Letters Patent is hereby corrected as shown below:

In Column 16, Line 19, in Claim 1, delete "electing" and insert -- selecting --, therefor.

In Column 16, Line 60, in Claim 4, delete "σis" and insert -- σ is --, therefor.

In Column 18, Line 22, in Claim 17, delete "a" and insert -- in a --, therefor.

In Column 19, Line 9, in Claim 21, delete "qual" and insert -- equal --, therefor.

Signed and Sealed this
Eleventh Day of December, 2012

David J. Kappos
*Director of the United States Patent and Trademark Office*